United States Patent [19]

Siclari et al.

[11] 4,218,384

[45] Aug. 19, 1980

[54] OMEGA-AMINO ALKENOIC ACIDS

[75] Inventors: Francesco Siclari, Barlassina Milan; Pietro P. Rossi, Garlasco Pavia, both of Italy

[73] Assignee: SNIA VISCOSA Societa Nazionale Industria Applicazioni Viscosa S.p.A., Italy

[21] Appl. No.: 885,608

[22] Filed: Mar. 13, 1978

Related U.S. Application Data

[62] Division of Ser. No. 486,992, Jul. 10, 1974, Pat. No. 4,085,127.

[30] Foreign Application Priority Data

Jul. 11, 1973 [IT] Italy ............................. 26479 A/73

[51] Int. Cl.$^2$ ........................... C09F 5/00; C11C 3/00
[52] U.S. Cl. ............................... 260/404; 260/18 R; 260/407
[58] Field of Search ........................................ 260/404

[56] References Cited

U.S. PATENT DOCUMENTS

| | | | |
|---|---|---|---|
| 2,777,873 | 1/1957 | Hasek | 260/404 X |
| 3,856,833 | 12/1974 | Siclari | 260/404 |
| 3,865,853 | 2/1975 | Hinze | 260/409 |
| 3,933,873 | 1/1976 | Love | 260/404 |

OTHER PUBLICATIONS

Morrison and Boyd, "Organic Chemistry," 3rd Ed. (1975), p. 674.
Delpierre et al., Chem. Absts., vol. 65, No. 18590d (1966).

*Primary Examiner*—John F. Niebling
*Attorney, Agent, or Firm*—Shlesinger, Fitzsimmons & Shlesinger

[57] ABSTRACT

An omega-amino alkenoic acid containing from 8 to 12 carbon atoms is obtained from an omega-formyl alkenoic acid, which also contains from 8 to 12 carbon atoms, by reacting the acid with ammonia and hydrogen in the presence of a hydrogenation catalyst. Preferably the omega-formyl alkenoic acid is obtained by reacting a polyunsaturated hydrocarbon cycloolefin with ozone to form a mono-ozonide in solution with a polar solvent, the solution being in the form of a separable phase which can be transposed to form the starting omega-formyl alkenoic acid.

15 Claims, 9 Drawing Figures

OHC—CH$_2$—CH$_2$—CH=CH—CH$_2$—CH$_2$—COOH    T.Q. (NaCl)

FIG. 7

H$_2$N—CH$_2$—CH$_2$—CH$_2$—CH=CH—CH$_2$—CH$_2$—COOH    T.Q. (NaCl)

FIG. 7A

H₂N-CH₂-CH₂-CH₂-CH=CH-CH₂-CH₂-COOH  (NUJOL) (KBr)

FIG. 8

OMEGA-AMINO ALKENOIC ACIDS

This application is a division of our copending U.S. application Ser. No. 486,992, filed July 10, 1974, now U.S. Pat. No. 4,085,127.

This invention relates to omega-amino alkenoic acids and to a method for their production.

The amino acids of the present invention be made from omega-formyl alkenoic acids, whose production by partial ozonolysis of polyunsaturated cycloolefins is described and claimed in our above-noted U.S. application, the contents of which may be referred to if necessary for the purpose of better understanding the hereinafter disclosed invention. Thus it is preferred to prepare the amino acids of the present invention starting from polyunsaturated cycloolefins, of which a satisfactory availability exists.

These unsaturated products have important applications in polymers or copolymers whose specific and potential reactivity, due to the presence of double bonds, enables them to be used for the manufacture of products which in turn possess useful properties. Examples of such products are textile products possessing a high degree of dyeability and additives for antistatic agents or for resins, all of which is easily understandable by persons skilled in the art.

The present invention provides omega-amino alkenoic acids containing from 8 to 12 carbon atoms and also a method of producing an omega-amino alkenoic acid containing from 8 to 12 carbon atoms which method comprises reacting an omega-formyl alkenoic acid containing from 8 to 12 carbon atoms with ammonia and hydrogen in the presence of a hydrogenation catalyst to produce an omega-amino alkenoic acid. The omega-formyl alkenoic acid used as starting material in the above method is preferably obtained by reacting a polyunsaturated hydrocarbon cycloolefin with ozone to form a mono-ozonide, the reaction being carried out in a solvent system comprising a non-polar solvent and a polar solvent, comprising at least one carboxylic acid and at least one anhydride of a carboxylic acid, the concentration of said polyunsaturated cyclo-olefin in the reaction mixture being from 10% to 40% by weight, to form a solution of the monoozonide in the polar solvent, which solution is a separable phase, and subjecting the mono-ozonide to transposition in the presence of a catalyst comprising a carboxylic acid anhydride in admixture with an alkali metal salt or an organic base salt of a carboxylic acid or an alkali metal alcoholate. This method is described and claimed in our above-noted copending application.

Specifically the invention includes 12-amino-4,8-dodecadienoic acid, 12-amino-4-dodecanoic acid, 12-amino-8-dodecanoic acid, 8-amino-4-octenoic acid, 10-amino-4-decenoic acid and 10-amino-6-decenoic acid.

In the reactive ammination step the ammonia is preferably added to the omega-formyl alkenoic acid as a 15 to 35 percent aqueous solution. The ammonia is preferably reacted with the omega-formyl alkenoic acid to form the amine salt of the corresponding omega-imino alkenoic acid prior to reaction with hydrogen.

Preferably said amine salt of the omega-imino alkenoic acid is reacted with an alkali metal or alkaline earth metal base to form the alkali metal or alkenoic earth metal salt of the omega-imino alkenoic acid, prior to reaction with hydrogen.

Preferably, the alkali or alkaline earth metal base is lithium, sodium or potassium hydroxide or carbonate, or barium or calcium hydroxide or carbonate.

Preferably the hydrogenation catalyst employed is nickel in the form of a salt, pure supported metal, or a Raney nickel.

The hydrogenation is preferably carried out under a hydrogen partial pressure of from 1.1 to 50 atmospheres.

The hydrogenation is preferably carried out at a temperature of between 20° C. and 150° C.

Preferably, after the reaction with hydrogen, the alkaline reaction mixture is extracted with an organic solvent to remove impurities.

The solvent preferably comprises benzene, toluene, xylene or a chlorobenzene. Said solvent extraction prefereably removes an omega diamino olefin from the reaction mixture.

As is known, cyclododecatriene-1,5,9, and likewise cyclodecadiene and cyclooctadiene, are products that are obtained by known process of cyclization of butadiene, are currently available on the market and are supplied by refineries and industries which treat and process petroliferous products. These cycloolefins are in general transformed by the petroleum processing industries themselves, or by the utilizer industry, into the corresponding cyclomonounsaturated product. For example, cyclododecene is obtained, which is for example utilized for the production of conventional nylon 12.

The industrial utilization of starting materials which contain more than one saturation, to obtain, with high conversions, first acidic aldehydes and then amino acids and their derivatives is not known in the technical and patent literature of the art. Thus, at least within the limits of the applicants' knowledge, it can be held that no such technology existed previous to the present invention.

The compounds of the invention are unsaturated linear omega-amino acids containing from 8 to 12 carbon atoms. When obtained from 11-formyl-4,8-undecadienoic acid they correspond to the formula:

HOOC—CH$_2$—CH$_2$—CH=CH—CH$_2$—CH$_2$—CH=CH—CH$_2$—CH$_2$—CH$_2$NH$_2$

Clearly, the compounds that are obtained from other omega formyl alkenoic acids having 8 to 10 carbon atoms correspond to similar formulae, but residual acid indicated has 8 and 10 carbon atoms respectively.

The omega-formyl alkenoic acids for use in the present invention may be prepared from the starting polyunsaturated cycloolefins, e.g. cyclododecatriene, cyclodecadiene or cyclooctadiene (independently, as has been said, of the form or mixture of isomeric forms and also, in the specific case of cyclododecatriene, possibly in admixture with cyclododecadiene) by means of a sequence of steps and operations during which not more than one unsaturation is removed, the said sequence comprising a selective ozonization from which is obtained the mono-ozonide which is then converted by transposition into the omega-formyl alkenoic acid, in the case in point 11-formyl-4,8-undecadienoic acid (as well as 11-formyl-4-undecenoic acid or 11-formyl-8-undecenoic acid and their mixtures) 7-formyl-4-heptenoic acid, 9-formyl-4-nonenoic acid and 9-formyl-6-nonenoic acid.

In the course of the detailed description that follows, referred to various examples of execution of the invention, certain omega-amino alkenoic acids and their possible uses are described.

The invention includes the conversion of the omega-amino alkenoic acid to omega-amino alkanoic acids, e.g. with hydrogen and palladium, under conventional conditions for this type of hydrogenation.

For example, from 12-aminododecadienoic acid there can be obtained 12-aminododecanoic acid, utilizable for the production of nylon 12. Similarly, from 8-aminooctenoic acid and from 10-aminodecenoic acid there can be obtained respectively 8-amino-octanoic acid and 10-aminodecanoic acid, which are utilizable for the production of nylon 8 and nylon 10 respectively. From the omega-amino-alkenoic acid there can be obtained interesting unsaturated polyamides, which are characterized by comprising at least one double bond C=C in their recurring monomeric units.

Over and above these, the method of the present invention provides, as by-products, the 1,12-dodeceda-4,8-diene-diamine and 1,12-dodecandioic acid. For these, by polycondensation, there is obtained -unsaturated 12, 12 nylon, or by hydrogenation of the olefinic unsaturations and subsequent polycondensation,-unsaturated 12, 12 nylon.

To further describe the present invention, there is hereafter set out a detailed exemplification of methods of obtaining the novel products according to the invention. This disclosure is completed by the annexed drawings, in which:

FIGS. 3 to 8 show a number of IR and NMR spectra in respect to certain unsaturated compounds obtainable according to the invention, in particular:

Figure 3:
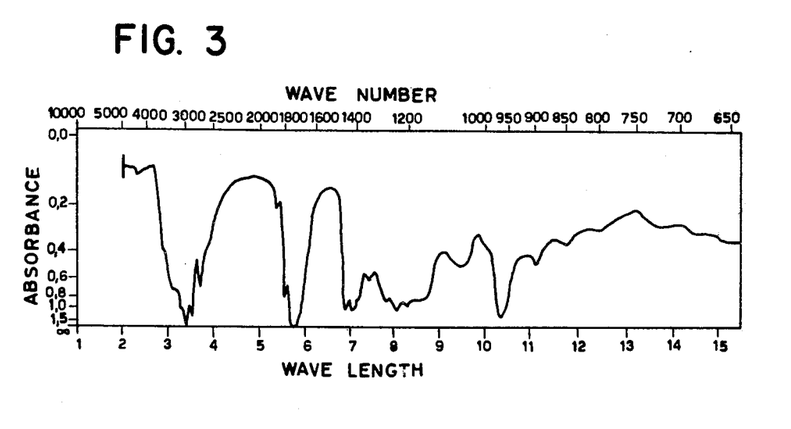
FIG. 3 shows the IR spectrum of 11-formyl-t, t-4,8-undecadienoic acid.
Figure 4:
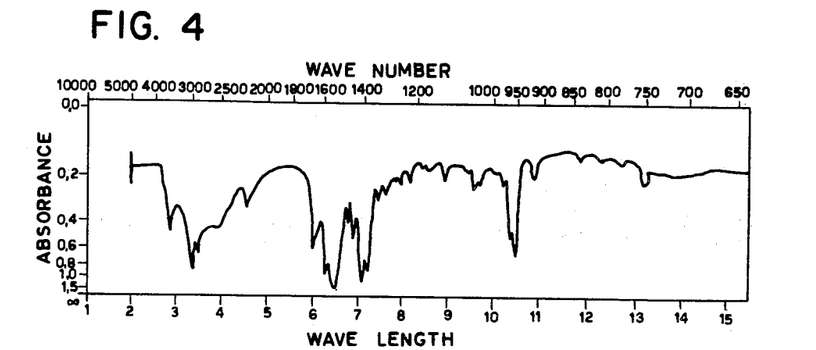
FIG. 4 shows the IR spectrum of 12-amino t, t-4,8-dodecadienoic acid obtainable by amination of the acid of FIG. 3.
Figure 5:
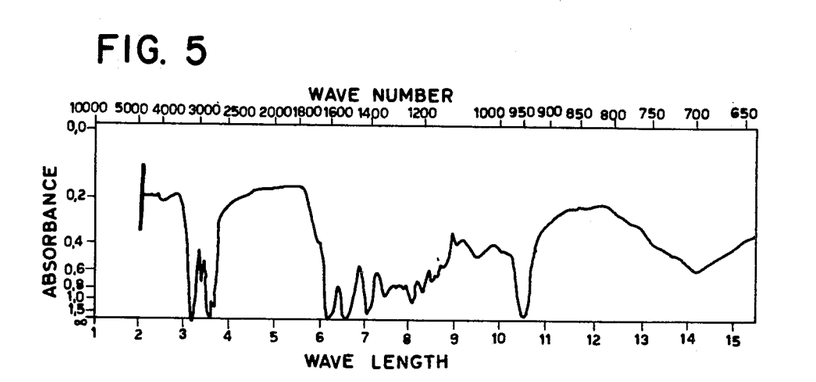
FIG. 5 shows the IR spectrum of the unsaturated polyamide as obtained from the said amino acid.

Examination of these spectra clearly reveals the following; for the group represented by FIG. 3 to FIG. 5 the band of the trans double bond (960 cm$^{-1}$) is preserved; the conversation of both 12 and 8 acidic aldehyde to unsaturated amino acid leads to the disappearance of the band typical of the aldehydes (C—H at approximately 2700 cm$^{-1}$) and to the appearance of the bands characteristic of the —NH$_3^\oplus$ (approximately 2200 cm$^{-1}$) of the amino acids, while in FIG. 5 which represents the 12-unsaturated polyamide there no longer appears the —NH$_3^\oplus$ band whereas there do appear the bands characteristic of the polyamides.

Figure 6:
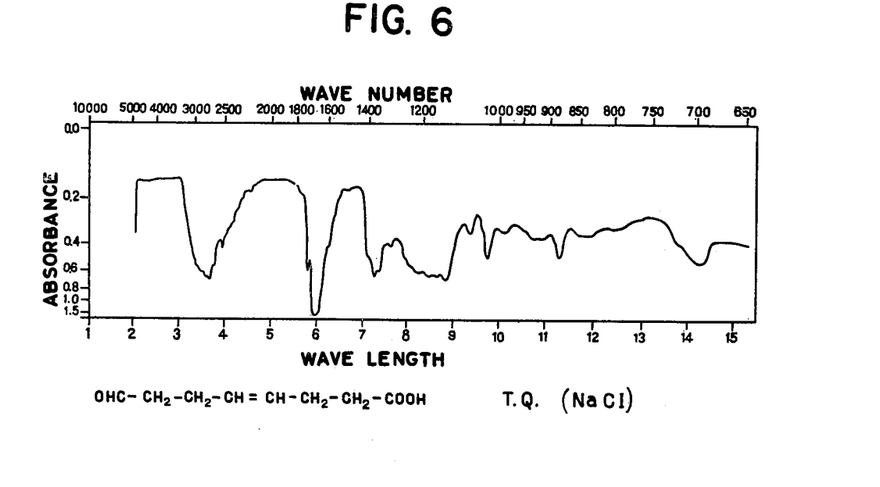
FIG. 6 shows the IR spectrum of 7-formyl-cis-4-heptenoic acid.
Figure 7:
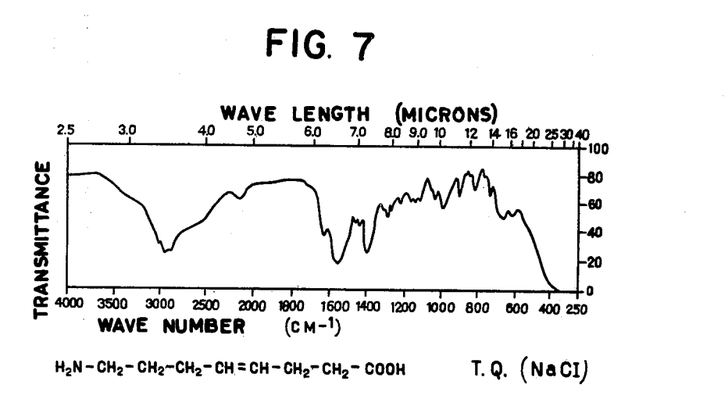
FIGS. 7 and 7/A, show the IR spectra, obtained by two different methods, of 8-amino-cis-4-octenoic acid.
Figure 7A:
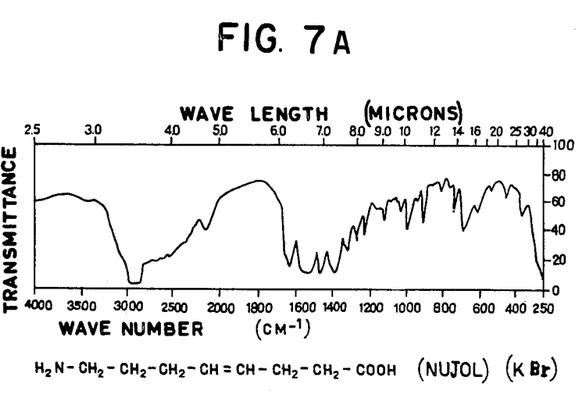
Figure 8:
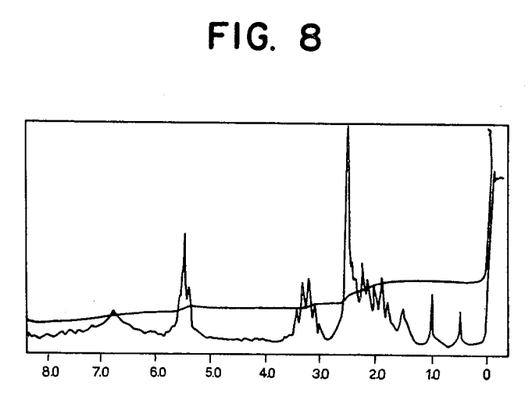
FIG. 8 shows the NMR spectrum of 8-amino-cis-4-octenoic acid.

In the group from FIG. 6 to FIG. 8, which represent the 8-unsaturated acidic aldehyde and the corresponding 8-unsaturated amino acid obtained from the cis, cis-1,5-cyclooctadiene, the cis band between 680 and 740 cm$^{-1}$ is preserved, while there are clearly visible the bands characteristic of the aldehyde group and of the protonic amino group of the amino acids respectively (approximately 2200 cm$^{-1}$).

In the NMR spectrum of the 8-amino-cis-4-octenoic acid dissolved in CF$_3$COOH there is confirmed the presence of the —NH$_3^\oplus$ group (broadened peak centred at 3.23, integration =3H) and of the cis double bond (peak centred at 4.53, integration =2H).

In the ensuing description specific indication will be given of the stereoisomeric forms and their proportions in the mixtures utilized, in the interests of greater bearing on the industrial field, in view of the availability on the market of polyunsaturated cycloolefins, e.g. cyclododecatriene, cyclodecadiene and cyclooctadiene in various stereoisomeric forms.

In the IR spectra shown in FIGS. 3 to 5, on the other hand, 1,5,9-t,t,t-cyclododecatriene has been specified as starting material simply because the derivatives show clearly in the IR the trans isomerism of the double bond, without this in any way limiting the scope of the invention, while for the cyclooctadiene the material used was cis-cis-1,5-cyclooctadiene.

The method characteristic of the invention will be described hereinafter summarily in its industrial applications directed towards the manufacture of 12-aminododecenoic acid, in its turn destined after hydrogenation for the production of nylon 12 (which, although selected as example, is not restrictive inasmuch as the technology in question is applicable to nylons 8 and 10).

Clearly, the novel unsaturated products which are characteristic of the invention are in such cases merely in the form of intermediates for this complete process.

Figure 1:
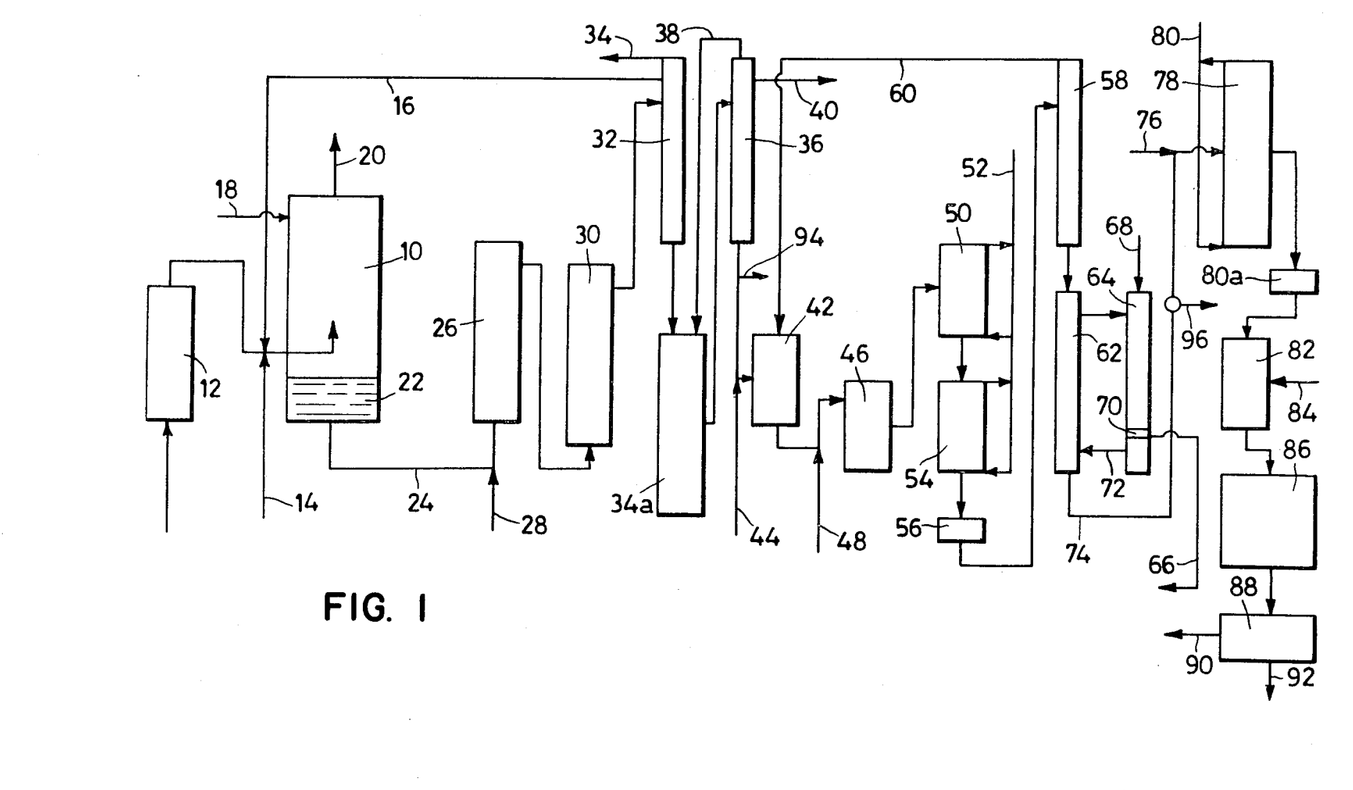
FIG. 1 shows schematically, in that the various components are individually well known, an installation utilizable for the preparation of 12-aminododecanoic acid from cyclododecatriene, that is to say of an important industrial product obtainable by hydrogenation of the unsaturated amino acid constituting what can at the present time be considered one of the principal products obtainable according to the invention.

The preparation of the starting omega formyl alkenoic acids, may be carried out for instance according to the method and apparatus schematically represented in FIG. 1. The initial step of treatment of the polyunsaturated cycloolefin with ozone is carried out in the vessel or reaction environment indicated generally by 10, in association with an apparatus 12 for production of ozone, after prior preparation of a stationary phase consisting of a mixture of high-boiling saturated hydrocarbon, preferably obtained from mineral oil (Vaseline (Vaseline is a Registered Trade Mark) oil or refinery cuttings) with a polar solvent, such as acetic acid, and-/or acetic anhydride. The ozone is used in the form of a mixture of O$_2$+O$_3$ containing from 5 to 80 grams, and prefereably from 15 to 60 grams of O$_3$ per cubic meter, or a mixture of O$_2$+O$_3$+CO$_2$ containing from 5 to 50 grams of ozone per cubic meter. Alternatively the ozone may be mixed with purified air stripped of nitrogen oxides by passing through sodium acetate dissolved in acetic acid or by passing over CuO and containing from 1 to 50 grams of O$_3$ per cubic meter. The ozonide is continuously deposited, as it is formed, in the container bottom as a heavy phase P formed by solution in the acetic acid and/or acetic anhydride. This stage may be carried out at any temperature comprised between 5° C. and 45° C. The acetic acid and/or acetic anhydride are fed into the apparatus at 14 and also recycled at 16. Cyclododecatriene is fed into the vessel continuously at 18, while at 20 the oxygen or other gas used as a vehicle for ozone is discharged.

The heavy phase 22 is metered and sent at 24 into the transposition apparatus 26 into which there is also metered at 28 an additional transposition catalyst, preferably sodium acetate, and possibly potassium acetate, sodium propionate or potassium propionate.

The transposition stage at 26 is carried out at a temperature ranging from 10° to 50° C., a solution of the unsaturated acidic aldehyde in acetic acid and/or acetic anhydride being obtained. Preferably, the transposition run is carried out progressively in a set of vessels, and in the embodiment of FIG. 1 this is achieved by transferring the solution to a second apparatus 30 from which the product is passed to an evaporator 32 the excess acetic acid is removed from the evaporator at 34 whereas the acetic acid and/or acetic anhydride which are distilled off are recycled at 16 into the ozonization vessel or environment 10. The temperature in the two transposition stages (26–30) can either be the same or it can be different. Usually it is higher in the vessel 30.

The anhydride of the acidic aldehyde left in the evaporator 32, is transferred to a hydroylsis apparatus 34a. The hydrolysis of the acidic aldehyde anhydride is carried out in this apparatus. Hydrolysis may be effected with water at a temperature of from 50° C. to 100° C. The solution is transferred to an evaporator 36, wherefrom the hydrolysis water is recycled at 38 into the hydrolysis apparatus 34a. A mixture of the excess water and possibly acetic acid is dumped, at 40. From the bottom of the evaporator 36 the acidic aldehyde is then discharged. An omega formyl alkenoic acid, obtained preferably as above mentioned, is introduced into an apparatus 42 for the formation of an imine (as exemplified hereinafter) which apparatus is fed at 44 with aqueous ammonia.

From the apparatus 42 the imine is withdrawn and transferred to an apparatus 46, fed at 48 with aqueous soda and Raney nickel, where the conversion is effected of the ammonium salt of the imine of the acidic aldehyde into the sodium salt of the same imine so as to give a compound more favorable to the subsequent reductive amination treatment.

The reaction mixture is transferred to an autoclave 50 for hydrogenating the imine, wherein hydrogen is introduced at 52, under recycling conditions, said hydrogenation being completed in a second autoclave 54.

After having been passed through a filter 56 for removing the catalysts, the ammonia solution of the sodium salt of the unsaturated amino acid is transferred to an evaporator 58 from which ammonia is distilled off (to be recycled at 60 into the imine formation apparatus 42).

The aqueous solution is then transferred into an extractor 62 where unsaturated diamine formed as secondary product is extracted with an appropriate organic solvent such as toluene, benzene, xylene or other solvents, and the light phase of this extraction is transferred to a separator 64 where the unsaturated diamine is reacted with carbon dioxide (fed in at 68), precipitated from its organic solution as carbamate and removed at 66. The carbamate is separated from the organic solvent by filtering through a filtering wall 70 and the organic solvent is recycled at 72 to the extractor 62.

The aqueous solution of the sodium salt of the unsaturated amino acid, treated in the extractor 62 is fed through a duct 74, with the addition at 76 of a hydrogenation catalyst (for example palladium), into a hydrogenation autoclave 78 which is fed at 80 with hydrogen under recycling conditions. The sodium salt of the saturated amino acid is thus obtained in aqueous solution.

The above indicated purification procedures as effected in the apparatus from 62 to 74 can be performed after the hydrogenation with palladium; in this case one obtains, as a by-product, the satureted diamine, in the form of the carbamate. The saturated or unsaturated diamine may be obtained by heating the corresponding carbonate.

The solution of the sodium salt, withdrawn from the autoclave 78, is passed through the filter 80a for removing the catalyst, is transferred to a suitable container 82, to which carbon dioxide is fed in at 84, and the whole mass is transferred to another vessel 86 where crystallization and/or washing of the amino acid takes place. The saturated amino acid is separated at 88 and discharged at 90, while the resultant mother liquors are removed at 92.

If one desires the unsaturated amino acid, for example for the production of unsaturated polyamides and in the case in point, unsaturated nylon-12, the latter can be withdrawn at 96 downstream of the extractor 62.

Figure 2:
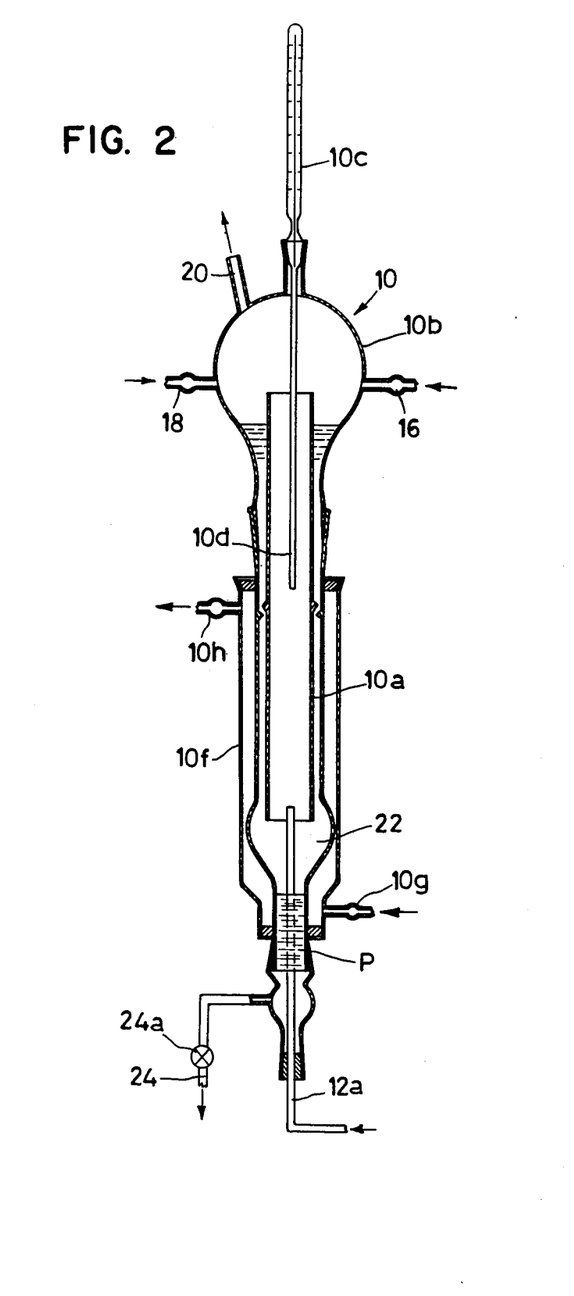
FIG. 2 shows in greater detail the equipment preferably used for the ozonization step.

The ozonization apparatus 10 is reproduced in detail, in a preferred embodiment, in FIG. 2 where the reference numerals connote like component parts as the same numbers in FIG. 1.

This apparatus comprises an internal reaction tube 10a, whose top end enters a flask 10b in which open the outlet 20 for the oxygen, and the ducts 18 for feeding in cyclododecatriene and 16 for feeding in the recycled acetic acid and/or anhydride. At 12a there is indicated the duct at the base of the reaction environment through which the product of the production of ozone ($O_2 + O_3$) producing apparatus 12 is introduced and at 24 there is indicated the discharge duct for the ozonide, equipped for a suitable valve 24a.

The apparatus is completed by an appropriate thermometer 10c whose sensitive bulb 10d is extended into the reaction tube. The portion in which reaction mainly occurs proper is cooled by an outer jacket 10f for an appropriate coolant mixture and having integral inlet and outlet fittings 10g, 10h.

There follow specific Examples describing parameters and conditions which are deemed more suitable for carrying out the invention with high yields.

EXAMPLES

Group I (Ozonization)

I(1) Ozonization of t,t,t-1,5,9-cyclododecatriene (CDT) in Acetic Acid-Acetic Anhydride-Paraffin Oil In this example there is described the preparation of the CDT mono-ozonide by ozonization in a mixed solvent, formed from acetic acid, acetic anhydride, and parrafin oil.

The CDT mono-ozonide can be employed to obtain unsaturated aldehyde acids, saturated and unsaturated dicarboxylic acids or polyaldehydes, which are useful products in themselves or for subsequent conversions.

In the vessel 10 of FIG. 1 there was charged 800 grams of t,t,t-1,5,9-cyclododecatriene (m.p.=30°–32° C.), purity 97.5%, 297 grams acetic acid, 503 grams acetic anhydride (purity 95.2%) and 6400 grams of paraffin oil. The temperature of the mixture was brought to 20° C. and 113.5 grams/hour of ozone in 1700 liters/hour of oxygen (at ambient pressures), 736 grams/hour of acetic anhydride, 585 grams/hour of acetic acid, 400 grams/hour of CDT and 80 grams/hour of paraffin oil were continuously fed into the vessel.

A heavy phase was continuously deposited on the bottom of the reactor vessel at the rate of 1900 grams/hour which phase consisted of CDT mono-ozonide dissolved in the acetic anhydride-acetic acid mixture.

After 16 working hours, 30410 grams of ozonide solution had been continuously discharged from the bottom of the reactor and sent to the transposition apparatus (No. 26, FIG. 1). The content of active oxygen (from iodometric assay according to Lohaus) was 37 mols overall, corresponding to 7760 grams of CDT ozonide as expressed in its classical form, the remainder being acetic anhydride, acetic acid and small quantities of cyclododecatriene and paraffin oil.

The total reacted cyclododecatriene (calculated from the amount charged, from what is left in the reactor and what is contained in the heavy phase) was 37.5 mols, a result which, as a rough estimate, indicates that CDT has reacted with ozone at a ratio of 1:1.

These data show that it is possible quantitatively to convert a polyunsaturated cycloolefin into its monoozonide. By employing paraffin oil, hydrocarbon losses in the reaction gas are prevented.

I(2) Ozonization of t,t,t-CDT in Acetic Acid-Acetic Anhydride Cyclohexane

In this example, the paraffin oil of Example I(1) was replaced by cyclohexane.

The Example I(1) was repeated employing cyclohexane in lieu of parraffin oil, and, in this case, too, a 1:1 reaction of CDT in ozone was obtained, although some cyclohexane was removed by the reaction gas and it was thus necessary to re-add it in the ozonizer.

I(3) Ozonization of cis,cis-1,5-cyclooctadiene

The Example I(2) was repeated, using cyclooctadiene (COD) as a polyunsaturated cycloolefin.

From the relative quantities of cycloolefin and ozone reacted it was seen that, in this case also, the ozone reacted in 1:1 molar ratio with the COD.

I(4) Ozonization of cis,trans-1,5-cyclodecadiene

The example I(2) was reated (using cyclodecadiene (CDD) as cycloolefin). In this case as well, a 1:1 reaction between olefin and ozone was found.

I(5) Ozonization of cis,t,t-CDT; cis,cis,t-CDT and t,t,t-CDT in Acetic Acid, Acetic Anhydride, Paraffin Oil The example I(1) was repeated, using a mixture of the various stereoisomers of CDT (70% of cis,t,t-CDT; 27% of t,t,t-CDT; 2% of cis, cis, t-CDT and 1% of cyclododecane.). The ozonizing gas consisted of a mixture of oxygen, ozone/carbon dioxide.

From the ozonization there was exclusively obtained the mono-ozonide of CDT.

I(6) Ozonization of Cyclododecadiene

Cyclododecadiene was used as the polyunsaturated olefin, in repeating the ozonization as described at I(1). The ozonide separated contained 95% of monoozonide of cyclododecadiene.

EXAMPLES

Group II (Transposition)

II(1) Transposition of the Mono-Ozonide of t,t,t-CDT into 11-Formyl-t,t-4,8-Undecadienoic acid The transposition of the CDT monoozonide into 11-formyl-t,t-4,8 indecadienoic acid may be carried out catalytically as described in the Examples that follow.

The ozonide solution (1900 grams/hour) coming from the apparatus 10 of FIG. 1, was sent continuously onto the bottom of a first transposition apparatus (26, FIG. 1) consisting of a 6-compartment steel cylinder fitted with thermometer, turbine type stirrer and temperature regulation jacket kept at 20° C. The transposition apparatus was also continuously fed with 4.75 grams/hour of sodium acetate dissolved in 42.8 grams of acetic acid. The mixture issuing from the top the first transposition apparatus passed to a second transposition apparatus (30, FIG. 1) which was the same as the first and was temperature-regulated at 30° C. Both the transposition apparatuses was kept under an inert gas atmosphere (carbon dioxide). The overall stay time was 7 hours and 30 minutes. Stirring was very slow.

Taking as equal to 100 the percentage of active oxygen (peroxidic oxygen) at the inlet of the first transposition apparatus, the analysis of this latter variable at the outlet of the first transposition apparatus was 31.7% and at the outlet of the second transposition apparatus was 7.6% (conversion 92.4%). The solution coming out of the second transposition apparatus was sent to a liquid-film evaporator (32, FIG. 1) to remove the solvents. The residue, 526 grams/hour, of a liquid oily at room temperature, is continuously treated at 72° C. with 526 grams/hour of water (stay time 60 minutes) in an inert gas (nitrogen) atmosphere (34, FIG. 1). The water was again evaporated as a liquid-film (36, FIG. 1). There was obtained 539 grams/hour of an oily residue which still contained small amounts of water, acetic acid and paraffin oil; it had the following characteristics:

| Aldehydic groups | 4.2 millimols/gram |
| Acidic groups | 4.5 millimols/gram |
| double bonds | 8.8 millimols/gram |

The product boiled at 180°–183° C. at a 3 mm of residual pressure, and consists of 11-formyl-t,t-4,8-undecadienoic acid.

II(2) Transposition of Ozonide of Cyclooctadiene

The example No II(1) was repeated, subjecting to transposition the mono-ozonide of cyclooctadiene (COD) obtained for instance as in Example I(3).

There was obtained 7-formyl-4-heptenoic acid, which on analysis showed the following characteristics:

| b.p. at 2.3 mm.Hg. = 146.5° C. $\eta_D^{20}$ = 1.4744 | | |
| --- | --- | --- |
| | calculated | found |
| double bonds (mmols from $H_2$/g. | 6.4 | 6.5 |
| -CHO-groups (titration with $H_2NOH \cdot HCl$) | 6.4 | 6.3 |
| -COOH groups (titration with NaOH) | 6.4 | 6.6 |

II(3) Transposition of the Ozonide of Cyclodecadiene

The example No. II(1) was repeated, transposing the monoozonide of cyclodecadiene (CDD) obtained for instance as in the Example I(4). There was obtained a mixture of 9-formyl-nonenoic acids, that is to say of 9-formyl-4-nonenoic acid and 9-formyl-6-nonenoic acid.

II(4) Transposition of the CDT Mono-Ozonide obtained from the Ozonization of mixtures of cis,t,t-CDT; cis,cis,t-CDT and t,t,t-CDT to 11-Formyl-4,8-Undecadienoic Acid The product is obtained in Example I(5) was subjected to transposition as described in Example II(1). An oily compound was obtained at a rate of 528 grams/hour, which was a mixture of the stearic isomers of 11-formyl-4,8-undecadienoic acid.

The product had a boiling point of 178° C.—185° C. under 3 mms of mercury.

II(5) Transposition of the Mono-Ozonide of Cyclododecadiene into 11-Formyl-4-Undecenoic Acid and 11-Formyl-8-Undecenoic Acid Example II(1) was repeated by effecting the transposition on the mono-ozonide of cyclododecadiene prepared for instance according to Example I(6). There have been obtained, in total, 515 grams/hour of 11-formyl-4-undecenoic acid and 11-formyl-8-undecenoic acid.

In the Examples of the preceding groups there has been shown the advantageous production of unsaturated acidic aldehyde suitable for use in the present invention. Following examples relate to the treatment of an acidic aldehyde, obtained preferably according to the teachings of our above-noted copending application, to obtain unsaturated products of the invention and also saturated compounds having a well known commercial importance.

EXAMPLES

Group III(Production of Unsaturated Amino Acids and Relative Unsaturated Nylons)

In this set of examples the possibility is shown of obtaining unsaturated amino acids from omega formyl alkenoic acids. The amino acids are important intermediates to obtain unsaturated nylons. There is also obtained as a by-product the unsaturated diamine which can easily be separated from the alkaline solution of the aminoacid by extraction with a solvent like benzene, toluene, or chloroform.

From the solution of the diamine in said solvents, the diamine may be recovered as carbamate by treatment with carbon dioxide. The diamine may be obtained by heating the carbamate.

The unsaturated amino acid is suitably obtained from its alkaline aqueous solutions by treatment with a weak acid, generally carbonic acid.

III(1) Reductive Amination of the Tranposition Product of the Ozonide of t,t,t-CDT into 12-Amino-t,t,4,8-Dodecadienoic Acid (by product: 1,12-Diamino-Dodecadiene-(4,8) and its Carbamate)

539 grams/hour of the transposition product of the CDT ozonide obtained for instance as disclosed in Example II(1), were continually fed to a vessel together with 2420 grams/hour of an aqueous solution of ammonia (28% $NH_3$) for the preparation of the ammonium salt of the imine of the unsaturated acidic aldehyde (42, FIG. 1). The temperature was maintained at 15° C.—20° C. by cooling; the stay time was one hour. The solution issuing from the apparatus for preparing the ammonium salt of the acidic aldehyde imine entered a second apparatus (46, FIG. 1) in which there were added 100 grams/hour of sodium hydroxide dissolved in 675 cu.cms water, which contained in suspension 33 grams of Raney nickel.

In this apparatus, the conversion of the ammonium salt of the imine of the unsaturated acidic aldehyde into the sodium salt thereof was completed by addition of sodium hydroxide.

The catalyst was maintained in suspension by vigorous stirring. This suspension was continuously fed to a first autoclave, (50, FIG. 1) maintained at a temperature of 95° C. and at a pressure of 30 atmospheres with hydrogen. The reaction time was 30 minutes.

The suspension emerging from the first autoclave entered a second autoclave (for completing the reaction) at 95° C. and 30 atmospheres (54, FIG. 1). The product issuing from the second autoclave was passed through a filter (56, FIG. 1) where the catalyst was collected and then into an evaporator under ambient pressure (58, FIG. 1) where the excess ammonia was stripped. The remaining solution was extracted continuously with toluene at 90° C.-95° C. (FIG. 1, Nos. 62 and 64).

The toluene extract was treated with $CO_2$ and the precipitate was collected by filtration at 70, FIG. 1. There were obtained 14 grams/hour of 1,12-diamino-dodecadiene-(4,8)-carbamate. Melting point 123.5° C.-128.5° C. (decomposition).

| | Calculated millimols/gram ($C_{13}H_{24}O_2N_2$) | Found millimols/gram |
|---|---|---|
| Amino groups | 8.34 | 8.37 |
| Double bonds | 8.34 | 8.20 |

By heating the diamine carbamate in toluene, the unsaturated diamine b.p.$_3$ = 130° C. was obtained. The aqueous phase was treated with carbon dioxide at zero °C. A precipitate was obtained of 230 grams/hour of unsaturated amino acid. The mother liquors were treated with ethanol and the sodium bicarbonate which precipitated was collected on a filter. The filtrate was concentrated in vacuo and treated at 0° C. with carbon dioxide again. 115 additional grams/hour of a precipitate was obtained which was combined with the first precipitate. The combined precipitates were crystallized from water and 298 grams/hour of unsaturated amino acid with m.p. of 190° C.-192° C. (12-amino-t,t-4,8-dodecadienoic acid) were obtained.

| | Calculated (mmols/gram) | Found (mmols/gram) |
|---|---|---|
| Total nitrogen | 4.74 | 4.67 |
| Primary aminic nitrogen | 4.74 | 4.69 |
| Double bonds | 9.48 | 9.37 |
| COOH Groups | 4.74 | 4.78 |

The separation of the unsaturated amino acid from the aqueous solutions coming from the reductive amination was not complete.

III(2) Reductive Amination of 7-Formyl-4-Heptenoic Acid to 8-Amino-4-Octenoic Acid Example No. III(1) was repeated, using 7-formyl-4-heptenoic acid, obtained for example as disclosed in the Example II(2) preparing the barium salt of the imine of the acidic aldehyde instead of the sodium salt so as to be able to separate, after amination, the barium as sulfate and leave the amino acid in aqueous solution, from which separation was performed by evaporation of the water.

After crystallization by means of propyl alcohol/ethyl acetate (60/40), there was obtained 8-amino-4-octenoic acid, m.p. 139°–144° C.

| Analysis | Calculated | Found |
|---|---|---|
| Primary Amino Groups (Van Slyke) | 6.36 | 6.4 |
| COOH groups (meq./NaOH/gram) | 6.36 | 6.4 |
| Double bonds (mmols $H_2$/g.) | 6.36 | 6.3 |

III(3) Reductive Amination of 9-Formyl Nonenoic Acids

Operation was carried out as described in the Example III(2) but using the unsaturated acidic aldehyde mixture obtained in the Example II(3); thereafter operating as described in the Example III(1), there was obtained a mixture of 10-amino-4-decenoic and 10-amino-6-decenoic acids.

III(4) Reductive Amination of the Transposition Product of the Ozonide of t,t,t-CDT to 12-Amino-t,t-4,8-Dodecadienoic Acid by Employing as the Catalyst Nickel as obtained by Decomposition of the Nickel Formate in Boiling Cyclododecane The purpose of this Example was to achieve reductive amination with a catalyst other than Raney nickel.

The procedure was the same as in Example III(1). The nickel was obtained by suspending the nickel formate in cyclododecane and slowly heating the suspension up to 230° C.–235° C.

This temperature was maintained until the evolution of decomposition gas was over.

By employing this catalyst there was obtained 305 grams/hour of an unsaturated amino acid (m.p. 189° C.–192° C.). The catalyst as obtained by decomposing the nickel formate in cyclododecane had an activity which equal to that of Raney nickel.

III(5) Reductive Amination of the Transposition Products of the Ozonide of cis,t,t-CDT and cis,cit,t-CDT and t,t,t-CDT to Unsaturated Amino Acid.

The procedure was as in III(1), but using unsaturated acid aldehyde obtained in Example II(4). There was obtained 285 grams/hour of mixtures of isomers of the 12-amino-4,8-dodecadienoic acid.

III(6) Reductive Amination of the Transposition Product of Cyclododecadiene Ozonide 11-formyl-4-undecenoic acid and 11-formyl-8-undecenoic acid as obtained in Example II(5) were subjected to reductive amination as in III(1). There was obtained 420 grams/hour of monounsaturated amino acid with a m.p. of 186° C.

The procedure of reductive amination according to the Examples from III(1) to III(4) can be applied also to the saturated acidic aldehydes as is hereafter exemplified. In such a case the separation of the amino acid, after the extraction of the saturated diamine may be performed by acidifying the alkaline salt or alkaline earth salt of the amino acid by means of a weak acid (carbonic acid) or by means of a strong acid (sulfuric acid) and separating the amino acid either by means of crystallization or by evaporation of the aqueous solvent.

Preparation of Omega Amino Alkanoic Acids from Omega Amino Alkenoic Acids.

EXAMPLES

Group IV

IV(1) Preparation of the 12-Aminododecanoic Acid from 12-Amino-t,t-4,8-Dodecanoic Acid The saturated amino acid, which represents the base product for the synthesis of the traditional nylons, was prepared by carrying out a catalytic hydrogenation with palladium on the solution of the unsaturated amino acid. The separation of the product is similar to that reported under III(1).

The procedure was as in III(1) and preceding Examples as regards the preparation of the unsaturated acidic aldehyde and the unsaturated amino acid.

30 grams/hour of 5% Pd on $Al_2O_3$ were slurried with the aqueous solution of the sodium salt of the 12-amino-t,t-4,8 dodecadiene acid coming from the extraction of the unsaturated diamine (at 76, FIG. 1).

The suspension was sent to an autoclave (78, FIG. 1), heated at 100° C. at a hydrogen pressure of 80 Atmospheres. After 3 hours and 30 minutes of reaction, the suspension issuing from the autoclave was filtered under heating to recover the catalyst (80, FIG. 1) and treated at 90° C. with $CO_2$ (82, FIG. 1). By cooling, the saturated amino acid crystallized (86, FIG. 1), and was separated by filtration (88, FIG. 1). It consisted of 403 grams/hour of product, m.p. 180°–182° C.

The mother liquors were acidified, pH 2, obtaining a precipitate of 21 grams/hour consisting of impure decandicarboxylic acid, the impurities being nitrogenous by-products.

IV(2) Preparation of 8-Amino-Octanoic Acid from 8-Amino Octenoic Acid

Operation was carried out as described in Example IV(1) effecting the hydrogenation of the double bond of the barium salt of the 8-amino octenic acid, obtained in Example III(2). In this case, the separation of the saturated amino acid was effected by precipitating the barium as sulphate, filtering and bringing the aqueous solution of the amino acid to dryness. By crystallization using propyl alcohol/$H_2O$ the 8-aminooctanoic acid, m.p. 190°–191° C. was obtained.

IV(3) Preparation of 10-Amino-Decanoic Acid from the 10-Amino-Decenoic Acids Operation was carried out as described in Example No. IV(1) effecting the hydrogenation of the double bond of the 10-amino-decenoic acids obtained in Example III(3). By performing the separation as described in the Example IV(2) 10-amino-decanoic acid, m.p. 185°–186° C. was obtained.

IV(4) Preparation of the 12-Amino-Dodecanoic Acid from the Unsaturated Amino Acid as obtained by Reductive Amination of the Transposition Products of the Monoozonide of Mixtures of CDT Isomers A saturated amino acid was prepared from stereoisomeric mixtures of unsaturated amino acids. The procedure was as in IV(1) employing the product obtained in III(5). There was obtained 408 grams/hour of 12-amino-dodecanoic acid, m.p. 179° C.–182° C.

IV(5) Preparation of the 12-Aminododecanoic Acid and of the 12-Amino-t,t-4,8-Dodecadienoic Acid The method of preparation of the saturated amino acid was modified, by separating that fraction of unsaturated amino acid which is obtained by treatment with $CO_2$ at 0° C. of the alkaline solutions of the unsaturated amino acid.

Example III(1) was repeated. Upon extraction of the unsaturated diamine, the solution of the sodium salt of the 12-amino-t,t-4,8-dodecadienoic acid was treated at 0° C. with $CO_2$. There was obtained by crystallization 245 grams/hour of unsaturated amino acid, m.p. 188° C.–190° C. The remaining solution was hydrogenated as in Example IV(1) and 162 grams/hour of saturated amino acid were thus obtained, m.p. 180° C.–182° C.

IV(6) Preparation of Dodecamethylene-diamine and 12-Amino-dodecanoic Acid

This Example describes the preparation of the saturated diamine and the saturated amino acid. The procedure was the same as in Example III(1). The solution of the sodium salt of the 12-amino-t,t-4,8-dodecadienoic acid and of 1,12-diamino-dodecadiene-(4,8) was supplemented with the palladium catalyst and hydrogenated as in Example IV(1). The hydrogenated product was extracted with toluene and treated with $CO_2$ as in Example III(1) while the residual solution was treated with $CO_2$ as in Example IV(1). There was obtained 15.1 grams/hour of dodecamethylenediamine carbamate and 401 grams/hour of 12-aminododecanoic acid.

IV(7) Preparation of 12-Aminododecanoic Acid

This saturated amino acid was prepared from the unsaturated amino acid purified and dissolved in an organic solvent. A 100 gram sample of 12-amino-t,t-4,8-dodecadienoic acid was dissolved in 900 grams of a solution of water/n-propanol (1:1). 5 grams of palladium on alumina were added and hydrogenated for 2 hours at 100° C.–30 Atm. After filtration of the catalyst by cooling, of 91 grams of 12-aminododecanoic acid, m.p. 181°–183° C. were crystallized.

IV(8) Polycondensation of 12-Aminododecanoic Acid 20 grams of saturated amino acid were polycondensed as described in the Example IV(10) hereinafter.

There were obtained 18.1 grams of polymer having intrinsic viscosity of 1.28 in m-cresol.

IV(9) Polycondensation of 8-Amino-Octanoic Acid 10 grams of 8-amino-octanoic acid were polycondensed as described in the Example IV(10) hereinafter.

There was obtained 9.1 grams of polymer having intrinsic viscosity of 1,2 in m-cresol.

IV(10) Polycondensation of the 12-Amino-t,t-4,8-Dodecadienoic Acid 20 grams of unsaturated amino acid with m.p. 190° C.–192° C. were polycondensed at 210° C. for 6 hours in an atmosphere of pure nitrogen.

There was obtained 18.2 grams of a polymer having a glossy ivory white color. Analysis of polymer: double bonds (catalytic hydrogenation in hexamethylphosphoramide=9.2 millimols/gram); m.p. (DSC)=189° C. Intrinsic viscosity (m-cresol)=1.2.

Having thus described our invention, what we claim is:

1. An omega amino alkenoic acid containing from 8 to 12 carbon atoms, and selected from the group consisting of 12-amino-4,8-dodecadienoic acid, 12-amino-4-do-decenoic acid, 12-amino-8-dodecenoic acid, 8-amino-4-octenoic acid, 10-amino-4-decenoic acid, 10-amino-6-decenoic acid, and mixtures thereof.

2. An acid as defined in claim 1 consisting of 12-amino-dodeca-4,8-dienoic acid, selectively in its stereoisomeric form having both the olefinic unsaturations of trans type or in its stereoisomeric form having one of the olefinic unsaturations of trans type and the other of cis type, or in the form of mixture of acids of said stereoisomeric forms.

3. A method of producing an omega amino alkenoic acid containing from 8 to 12 carbon atoms by the reductive amination of an omega formyl alkenoic acid, comprising reacting an omega formyl alkenoic acid containing from 8 to 12 carbon atoms with ammonia and hydrogen in the presence of a hydrogenation catalyst.

4. A method as defined in claim 3, including
    subjecting a solution containing a cyclo-olefin, having from 8 to 12 carbon atoms, in a concentration of from about 10% to 40% by weight, and having more than one unsaturation, to a selective ozonization step in the presence of a solvent mixture of at least one non-polar solvent, at least one polar solvent, and an organic acid anhydride, with the weight ratio of said anhydride to the polar solvent being set at between 1:2 and 2:1, whereby the mono-ozonide of said cycloolefin is obtained,
    subjecting said mono-ozonide to at least one transposition step, to obtain the corresponding omega formyl alkenoic acid and
    reacting said omega formyl alkenoic acid with ammonia and hydrogen in the presence of a hydrogenation catalyst.

5. A method as defined in claim 3, including treating the omega formyl alkenoic acid with ammonia to form the ammonium salt of the corresponding omega imino alkenoic acid before effecting the reaction with hydrogen.

6. A method as defined in claim 5, wherein the salt of the omega imino alkenoic acid is transformed, prior the reaction with hydrogen, into the salt of an alkali metal or of an alkali earth metal by treatment with an alkali metal base or with an alkali earth metal base.

7. A method as defined in claim 6, wherein said alkali metal base is selected from the group consisting of sodium hydroxide, potassium hydroxide, lithium hydroxide, sodium carbonate, potassium carbonate, lithium carbonate, and said alkali earth metal base is selected from the group consisting of calcium hydroxide, barium hydroxide, calcium carbonate and barium carbonate.

8. A method as defined in claim 3, wherein the ammonia is in aqueous solution in a concentration of from 15% to 35% by weight.

9. A method as defined in claim 3, wherein the hydrogenation catalyst is nickel in the form selected from the group consisting of a nickel salt, pure nickel, supported nickel and Raney nickel.

10. A method as defined in claim 3, wherein the reaction with hydrogen is performed at a partial hydrogen pressure of from 1.1 to 50.0 atmospheres.

11. A method as defined in claim 3, wherein the reaction with hydrogen is performed at a temperature between 20° C. and 150° C.

12. A method as defined in claim 4, wherein the obtained omega amino alkenoic acid is subjected to a process of purification by extraction of the alkaline solution with an organic solvent at temperature from 20° C. to 100° C.

13. A method as defined in claim 12, wherein said organic solvent is selected from the group consisting of benzene, toluene, xylenes and chlorobenzenes.

14. A method as defined in claim 6, including transforming the alkali metal salt or the alkali earth metal salt of omega amino alkenoic acid into the corresponding amino acid by treatment with an acid.

15. A method as defined in claim 14, wherein the last-named acid comprises carbonic or sulphuric acid.

* * * * *